United States Patent [19]
Zvenyatsky et al.

[11] Patent Number: 5,383,888
[45] Date of Patent: Jan. 24, 1995

[54] ARTICULATING ENDOSCOPIC SURGICAL APPARATUS

[75] Inventors: Boris Zvenyatsky, Bronx, N.Y.; Ernest Aranyi, Easton; H. Jonathan Tovey, Milford, both of Conn.

[73] Assignee: United States Surgical Corporation, Norwalk, Conn.

[21] Appl. No.: 834,687

[22] Filed: Feb. 12, 1992

[51] Int. Cl.[6] .................................. A61B 17/28
[52] U.S. Cl. .................................. 606/206; 606/205; 606/170; 606/174; 128/751
[58] Field of Search ............... 606/205, 206, 207, 170, 606/174; 128/751

[56] References Cited

U.S. PATENT DOCUMENTS

| | | | |
|---|---|---|---|
| 1,127,948 | 2/1915 | Wappler | 606/170 X |
| 1,620,828 | 3/1927 | Molony . | |
| 2,028,635 | 1/1936 | Wappler . | |
| 2,113,246 | 5/1937 | Wappler . | |
| 3,314,431 | 4/1967 | Smith, Jr. . | |
| 3,667,474 | 6/1972 | Lapkin et al. . | |
| 3,788,303 | 1/1974 | Hall . | |
| 3,892,228 | 7/1975 | Mitsui . | |
| 4,672,964 | 6/1987 | Dee et al. | 606/170 |
| 4,688,555 | 8/1987 | Wardle . | |
| 4,763,669 | 8/1988 | Jaeger . | |
| 4,872,456 | 10/1989 | Hasson . | |
| 4,880,015 | 11/1989 | Nierman . | |
| 4,941,455 | 7/1990 | Watanabe et al. . | |
| 4,944,741 | 7/1990 | Hasson . | |
| 4,947,827 | 8/1990 | Opie et al. . | |
| 4,950,273 | 9/1990 | Briggs | 606/174 X |
| 5,152,279 | 10/1992 | Wilk . | |
| 5,174,300 | 12/1992 | Bales et al. | 606/205 X |
| 5,195,506 | 3/1993 | Hulfish | 128/20 |
| 5,209,747 | 5/1993 | Knoepfler | 606/16 |

FOREIGN PATENT DOCUMENTS

| | | |
|---|---|---|
| 0449663 | 10/1991 | European Pat. Off. . |
| 0484671 | 5/1992 | European Pat. Off. . |
| 3303335 | 8/1984 | Germany . |
| 8711051 | 2/1988 | Germany . |
| 101674 | 4/1988 | Germany . |
| 9007356 | 6/1991 | Germany . |
| 9109097 | 10/1991 | Germany . |
| 9300161 | 4/1993 | Germany . |
| 980703 | 12/1982 | U.S.S.R. ........................ 606/174 |
| 990220 | 1/1983 | U.S.S.R. . |

OTHER PUBLICATIONS

European Search Report for EP Appln. No. 93 10 2141.
European Search Report for EP Appln. No. 93 11 2520.
"Levy Articulating Retractor", *Surgical Products*, p. 33, Jun. 1992 edition.

*Primary Examiner*—Richard J. Apley
*Assistant Examiner*—Beverly A. Meindl

[57] ABSTRACT

A surgical instrument is provided for use in endoscopic or laparoscopic surgery. The instrument includes a handle portion and an endoscopic portion. The endoscopic portion has an elongated tubular section having opposed proximal and distal ends, the proximal end of which extends from the handle portion, and an articulating section which is pivotally connected to the tubular section adjacent the distal end thereof. Tool means depend from the articulating section and a linkage mechanism is associated with the endoscopic portion for pivoting the articulating section relative to the longitudinal axis of the tubular section, within a 90° sector of rotation. In addition, the instrument includes means for rotating the endoscopic portion about its longitudinal axis.

47 Claims, 12 Drawing Sheets

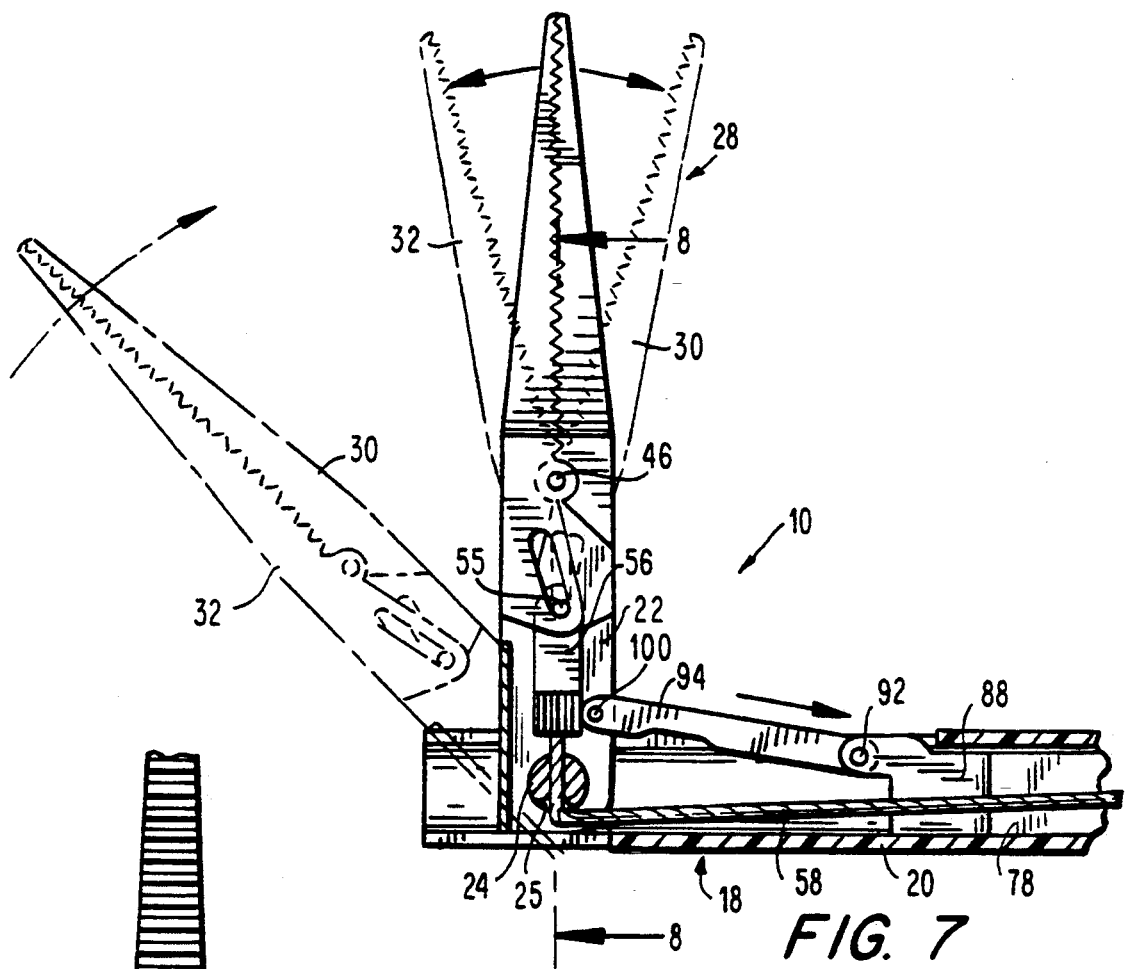
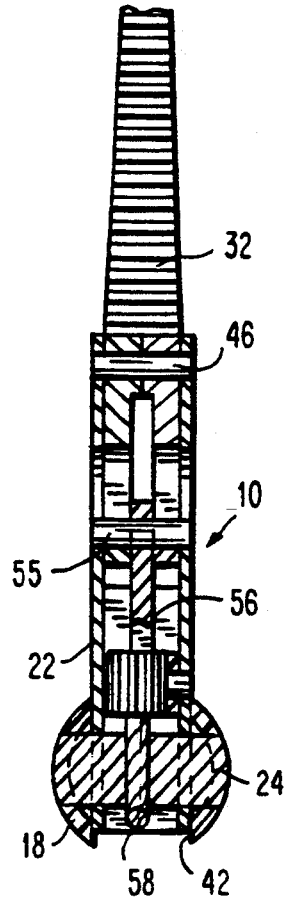
FIG. 7
FIG. 8

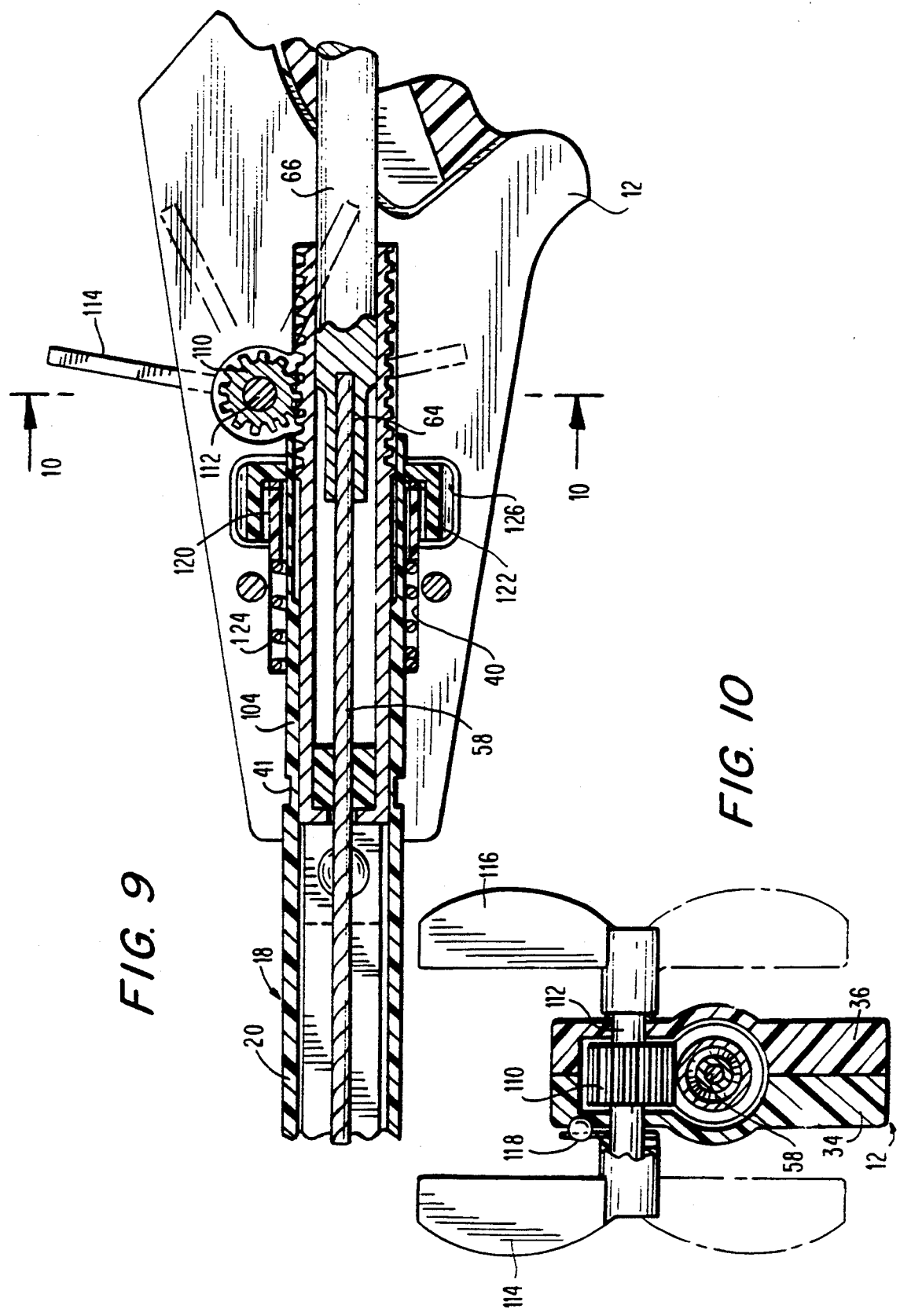

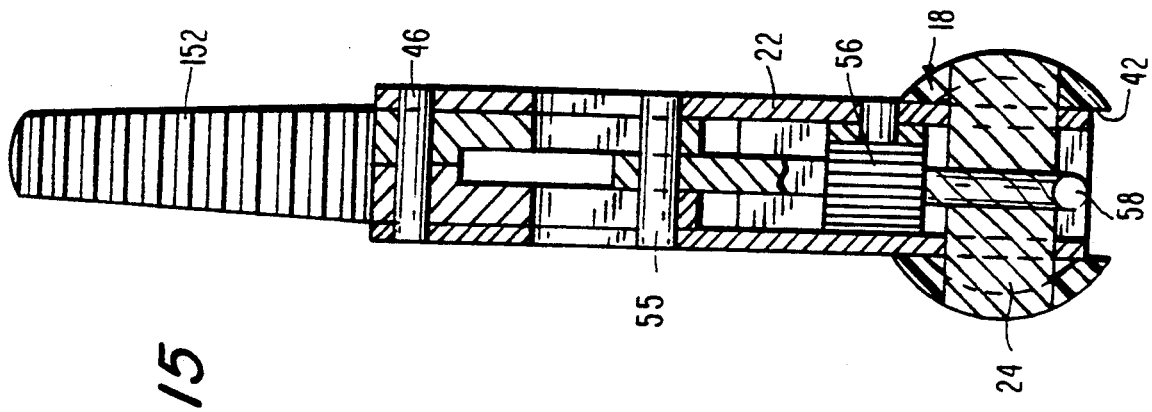
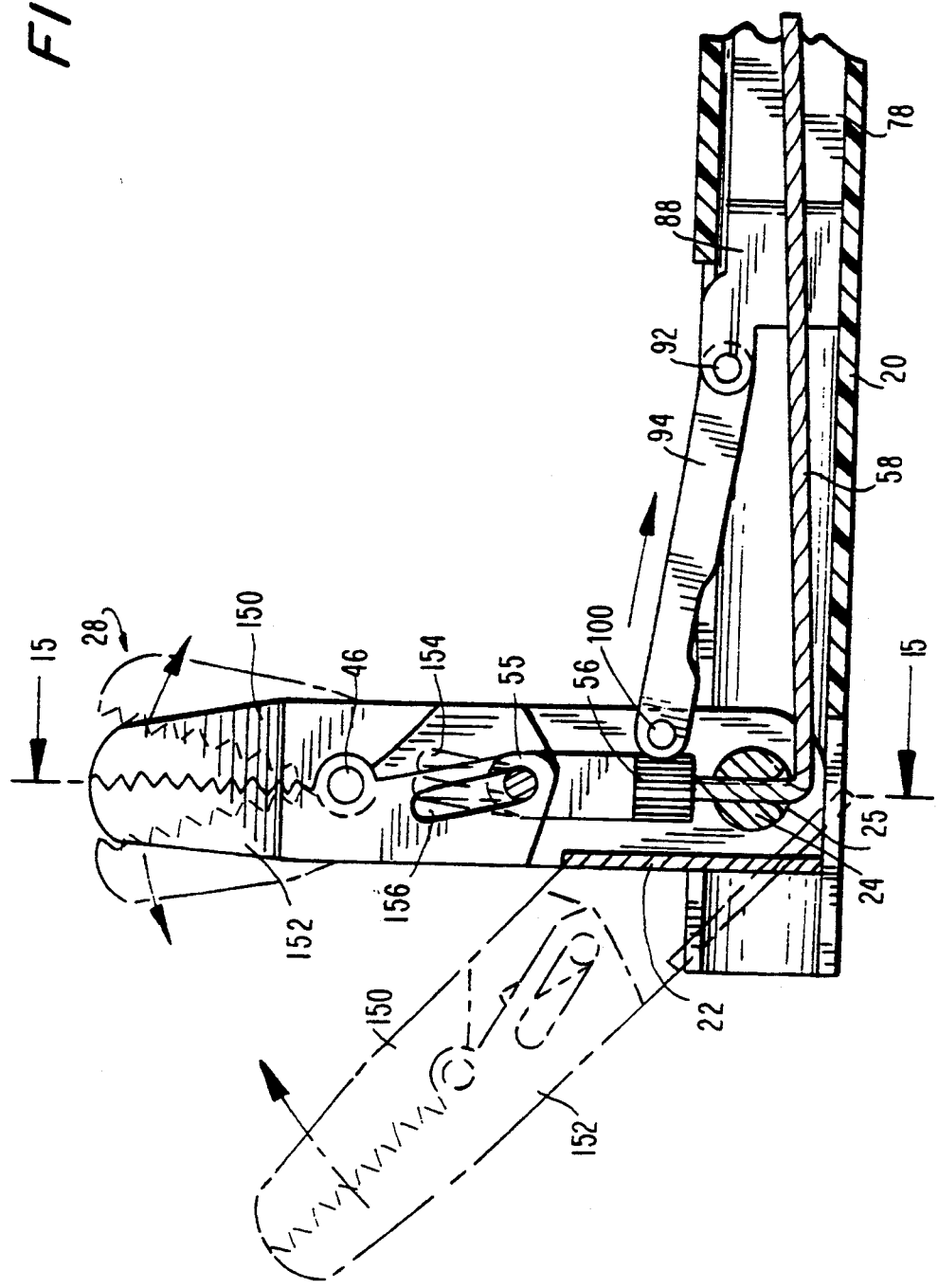

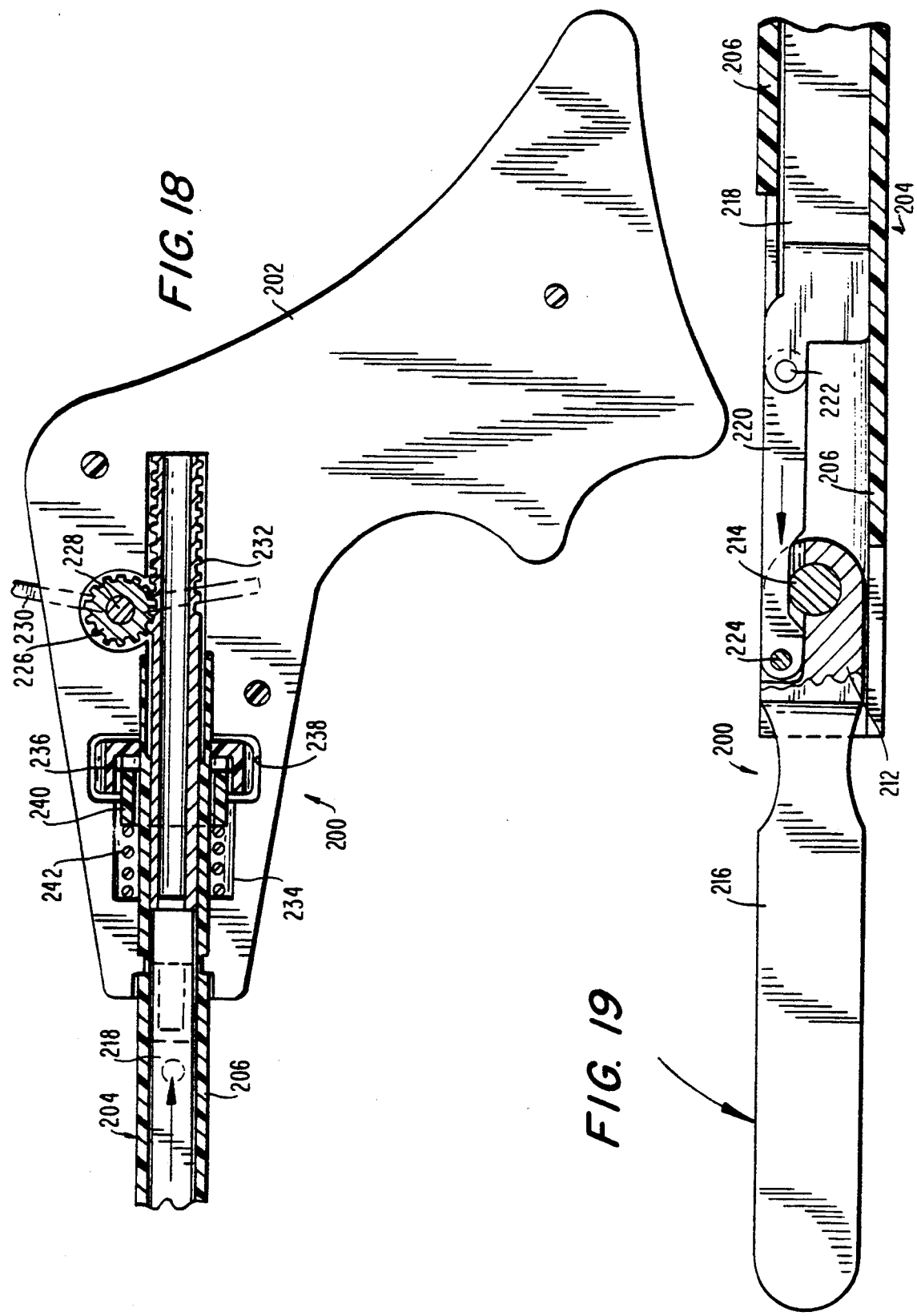

ARTICULATING ENDOSCOPIC SURGICAL APPARATUS

BACKGROUND OF THE INVENTION

1. Field of the Invention

The subject invention relates to surgical apparatus for performing laparoscopic and endoscopic surgical procedures, and more particularly to apparatus having an end portion which can be articulated in a patient's body during a surgical procedure.

2. Description of Related Art

In laparoscopic and endoscopic surgical procedures a small incision or puncture is made in the patient's body to provide access for a tube or a cannula device. Once extended into the patient's body, the cannula allows insertion of various surgical instruments such as scissors, dissectors or retractors to perform the surgery.

An example of an endoscopic surgical instrument is illustrated in U.S. Pat. No. 2,113,246 which issued to Wappler on Apr. 5, 1938. This patent discloses endoscopic forceps comprising an elongated conduit with jaws at the distal end thereof, a control rod in the conduit for controlling the operation of the jaws, and a control handle at the proximal end of the conduit which is operatively connected to the control rod. This surgical instrument is extremely limited in its application in that the angle of the conduit portion mounting the jaws cannot be adjusted in relation to the remaining portion of the conduit during a surgical procedure.

Improvements have been made in the art of surgical instruments to increase their range of operability. For example, U.S. Pat. No. 4,763,669 which issued to Jaeger on Aug. 16, 1988 discloses a microsurgery instrument with an adjustable angle of operation for obtaining cervical biopsies.

Similarly, U.S. Pat. No. 4,880,015 which issued to Nierman on Nov. 14, 1989 discloses a surgical device having an increased range of operability. In particular, this patent shows a biopsy forceps designed for use through a flexible fiberoptic bronchoscope. The biopsy forceps includes a handle connected to a thin elongated flexible shaft with a distal portion thereof hinged to the shaft. A grasping tool or biopsy forceps is attached to the distal hinged portion. Control wires extend from the handle to the distal end to the shaft for controlling the angular rotation of the distal portion of the instrument.

Of the references discussed above, none of these instruments disclose a laparascopic instrument for insertion into a body cavity through a cannula and adapted for a wide range of laparascopic surgical applications. Further, the instruments disclosed therein are not provided with means for rotating the tool head about the longitudinal axis of the endoscopic portion of the instrument. Instead, a surgeon using either of these prior art instruments must physically rotate the entire instrument in order to change the rotational orientation of the distal end of the conduit or tube.

Accordingly, it is an object of the subject invention to provide an endoscopic surgical instrument having a tool head which is independently moveable about two axes of rotation relative to the handle while the instrument is in use.

It is another object of the subject invention to provide a lightweight endoscopic surgical instrument which can provide a clearer line of sight for a surgeon during a surgical procedure.

It is still another object of the subject invention to provide an endoscopic instrument in which a wide variety of different tool heads may be employed.

It is yet another object of the subject invention to provide an endoscopic instrument which may be used to perform electrocauterization during surgical procedures.

Another object of the subject invention is to provide an endoscopic instrument which is inexpensive to manufacture.

These and other objects of the subject invention will be made more apparent from the following description taken in conjunction with the accompanying drawings.

SUMMARY OF THE INVENTION

An endoscopic surgical instrument is disclosed for use in a wide variety of roles including grasping, dissecting, clamping, or retracting materials or tissue during surgical procedures performed within a patient's body and particularly within the abdominal cavity.

The surgical instrument of the subject invention includes a handle portion having a fixed handle, and an endoscopic portion which depends from the handle portion. The endoscopic portion includes an elongated tubular section and an articulating section which is pivotally connected adjacent to the distal end of the tubular section. Tool means are operatively connected to the articulating section of the endoscopic portion. A linkage mechanism is associated with the endoscopic portion of the instrument for selectively pivoting the articulating section in an angular plane relative to the longitudinal axis of the tubular section within about a 90° sector of rotation. This linkage mechanism is preferably controllable from the handle portion of the instrument.

In a preferred embodiment of the subject invention, the surgical instrument may include a handle portion having a fixed handle and a pivoting handle. A cable extends from the pivoting handle through the endoscopic portion to the tool means. In this embodiment, the tool means may comprise a pair of cooperating jaws, the movement of which is controlled by operating the pivoting handle.

The linkage mechanism for pivoting the articulating section of the endoscopic portion preferably may include an elongated push rod extending from the handle portion, through the endoscopic portion. The push rod would be connected to a link member, which, in turn may be pivotally connected to the articulating section of the endoscopic portion. In addition, the linkage mechanism may include a reciprocating member having a gear rack disposed adjacent the handle portion of the instrument in cooperation with the proximal end of the elongated push rod. The gear rack member would be movable in an axial direction in response to rotation of an annular pinion gear in the handle portion of the instrument. Rotation of the pinion gear would cause the gear rack member to translate coaxially, causing the push rod to move, and thereby causing the articulating section of the endoscopic portion to pivot within a 90° sector of rotation relative to the longitudinal axis of the endoscopic portion of the instrument.

Preferred embodiments of the subject invention may also include means for rotating the endoscopic portion of the surgical instrument about the longitudinal axis thereof. In this instance, an annular bushing, which may be concentrically disposed within an annular cuff, would be provided in the handle portion of the instrument. The proximal end of the endoscopic portion of the instrument would be arranged within the bushing and would be rotatable about its longitudinal axis by rotating the annular cuff.

In an alternate embodiment of the subject invention, the surgical instrument may include a handle portion configured as a pistol-grip and an endoscopic portion including an elongated fixed tubular section which depends from the handle portion and an articulating section pivotally connected to the fixed section adjacent the distal end thereof. An elongated paddle tool would depend from the articulating section of the endoscopic portion for performing retraction tasks during surgical procedures. In addition, a linkage mechanism would be associated with the endoscopic portion of the instrument for pivoting the articulating section relative to the longitudinal axis of the fixed section, within a 90° sector of rotation. The instrument could also be provided with means for rotating the endoscopic portion thereof about its longitudinal axis.

Further features of the subject invention will become more readily apparent from the following detailed description of the invention taken in conjunction with accompanying drawings.

BRIEF DESCRIPTION OF THE DRAWINGS

Preferred embodiments of the subject invention will be described hereinbelow with reference to the drawings, wherein:

FIG. 7 is a side cross-sectional view showing, in solid and in phantom lines, the various pivoting movements of the articulating section of the endoscopic portion of the surgical instrument shown in FIG. 1.;

FIG. 8 is an enlarged side cross-sectional view of the distal end of the endoscopic surgical instrument taken along line 8—8 of FIG. 7;

FIG. 9 is an enlarged side cross-sectional view of the handle portion of the endoscopic surgical instrument illustrating the various positions of the pinon gear which comprises a portion of the linkage mechanism of the subject invention;

FIG. 10 is a front cross-sectional view taken along line 10—10 of FIG. 9;

FIG. 14 is a side cross-sectional view showing, in solid and in phantom lines, the pivotal movements of the articulating section of the endoscopic portion of the subject invention with the alternate embodiment of the tool head shown in FIGS. 11-13;

FIG. 15 is a front cross-sectional view taken along line 15—15 of FIG. 14;

FIG. 18 is a side cross-sectional view taken along line 18—18 of FIG. 16;

FIG. 19 is a side cross-sectional view taken along line 17—17 of FIG. 16;

DETAILED DESCRIPTION OF THE PREFERRED EMBODIMENT

Figure 1:
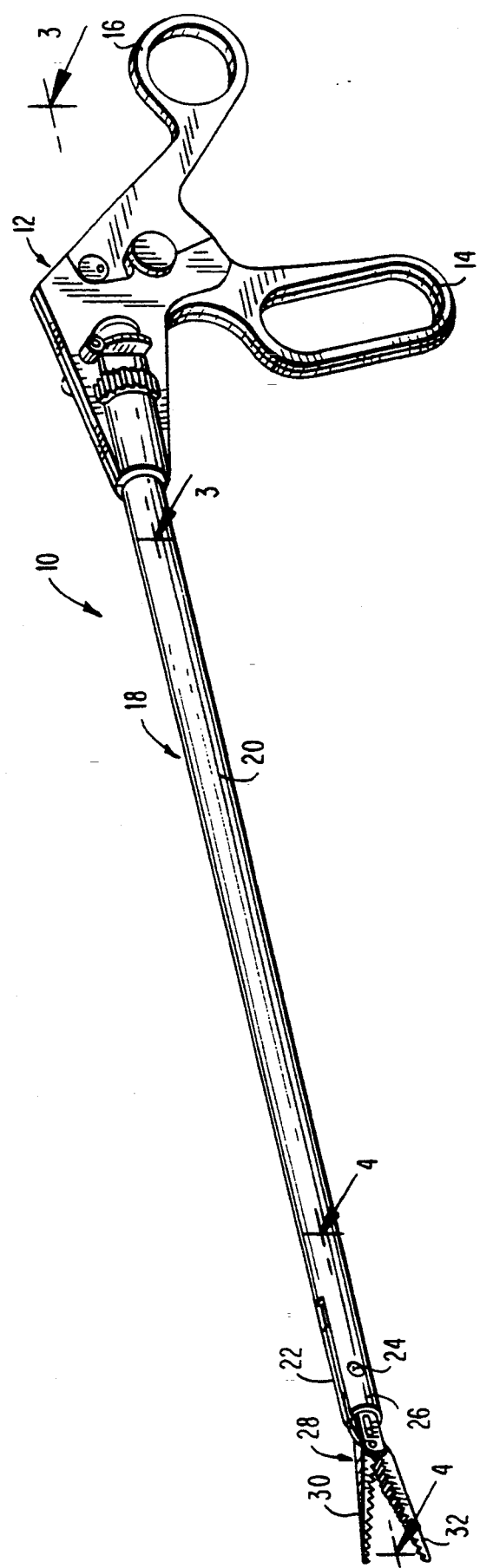
FIG. 1 is a perspective view of an articulating endoscopic surgical instrument in accordance with a preferred embodiment of the subject invention.

The articulating endoscopic surgical instrument of the subject invention is illustrated in FIG. 1 and is designated generally by reference numeral 10. Surgical instrument 10 comprises a handle portion 12 including a fixed handle 14 and a pivoting handle 16. An endoscopic portion 18 extends orthogonally from handle portion 12 and includes an elongated fixed tubular section 20 and an articulating section 22. The articulating section 22 is pivotally connected to the fixed section 20 by a pin 24 disposed adjacent the distal end 26 of section 22. A tool head 28 having cooperating jaws 30, 32 depends from the articulating section 22 and may be formed in a wide variety of configurations including graspers, dissectors, or clamps.

Figure 2:
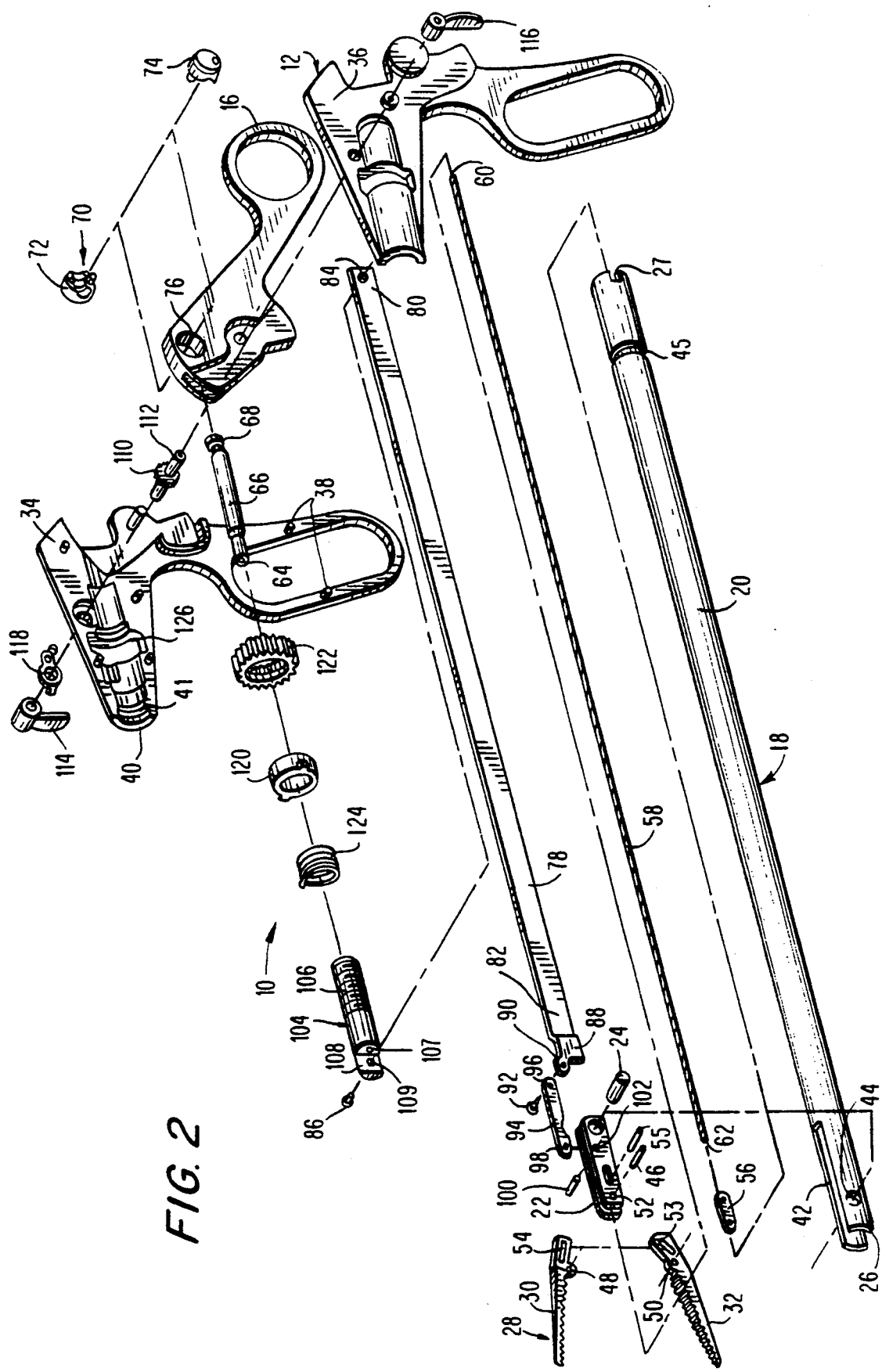
FIG. 2 is an exploded view of the articulating endoscopic surgical instrument of FIG. 1.

Turning to FIG. 2, the handle portion 12 and the associated fixed handle 14 comprises complimentary sections 34 and 36 which are mounted to one another by a plurality of bosses 38 formed on section 34. The plurality of bosses 38 are arranged for engagement in corresponding apertures (not shown), which are formed in section 36 of handle portion 12. In addition, each of the complimentary sections 34, 36 of handle portion 12 are formed with a portion of a stepped bore 40 which is provided therein for accommodating various components of the subject invention, all of which will be described in greater detail hereinbelow. Stepped bore 40 includes a circumferential flange 41 for securing the tubular section 20 of endoscopic portion 18 in handle portion 12.

Figure 4:
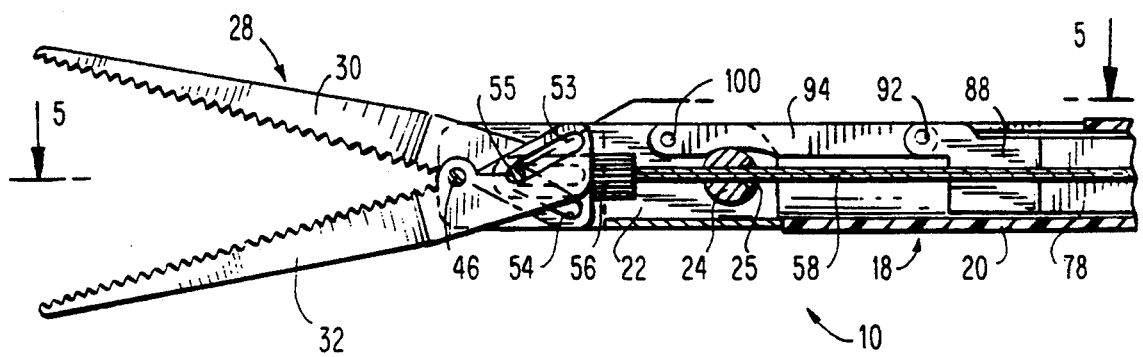
FIG. 4 is a side cross-sectional view taken along line 4—4 of FIG. 1 illustrating the distal end of the endoscopic surgical instrument.
Figure 5:
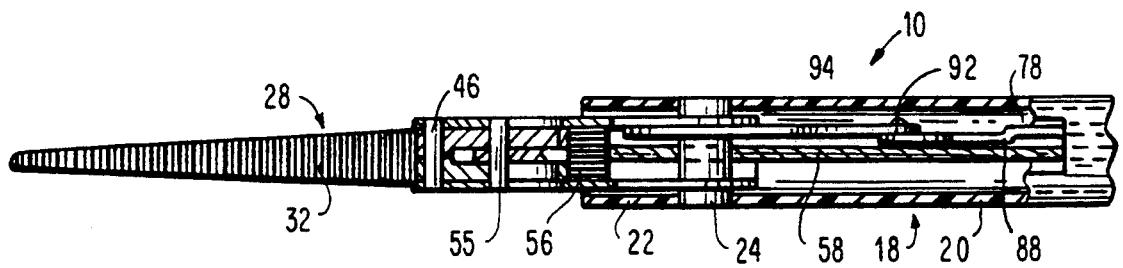
FIG. 5 is a top plan view cross-section view taken along line 5—5 of FIG. 4.
Figure 6:
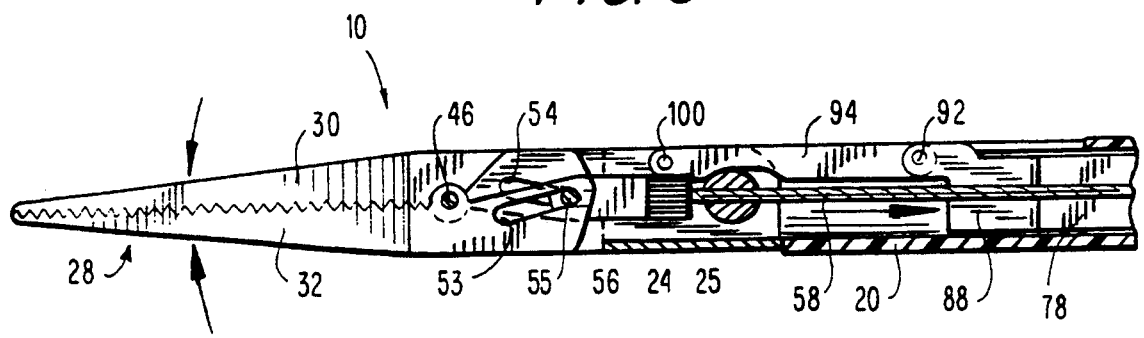
FIG. 6 is a side cross-sectional view of the distal end of the endoscopic surgical instrument showing the jaws in a closed position.
Figure 11:
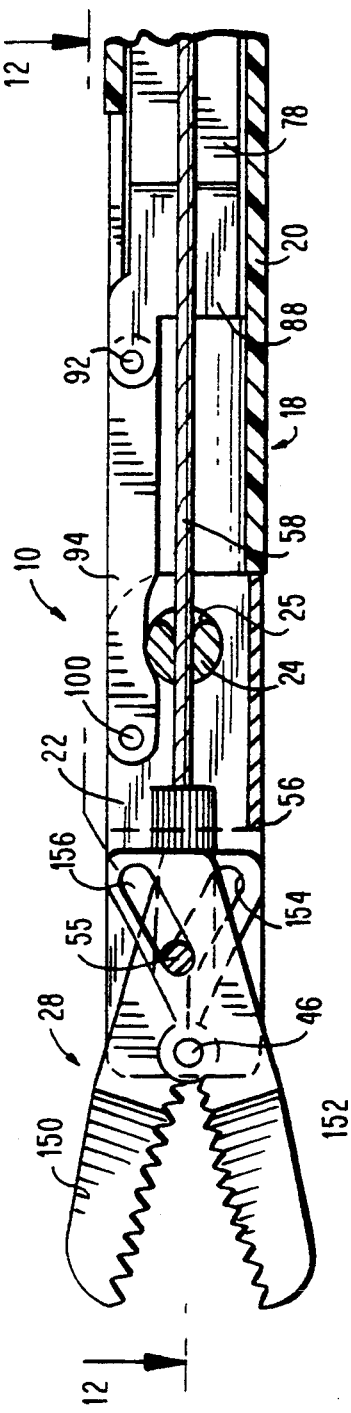
FIG. 11 is a side cross-sectional view illustrating an alternate embodiment of the tool head of the endoscopic surgical instrument of the subject invention in an open position.
Figure 12:
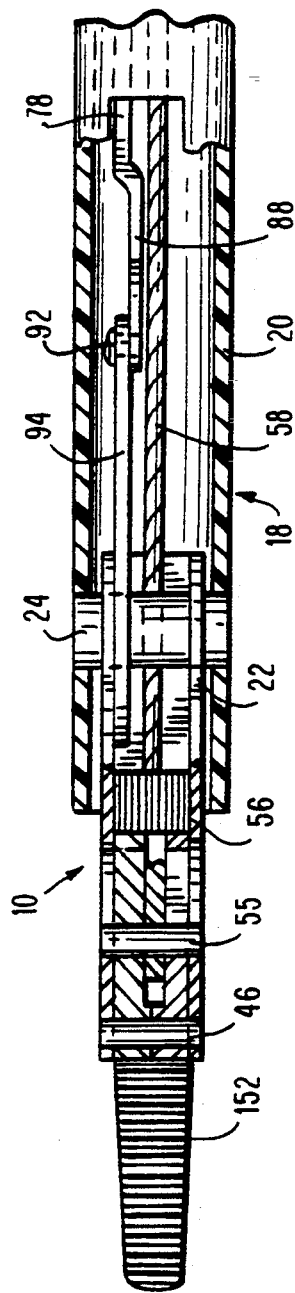
FIG. 12 is a top cross-sectional view taken along line 12—12 of FIG. 11.
Figure 13:
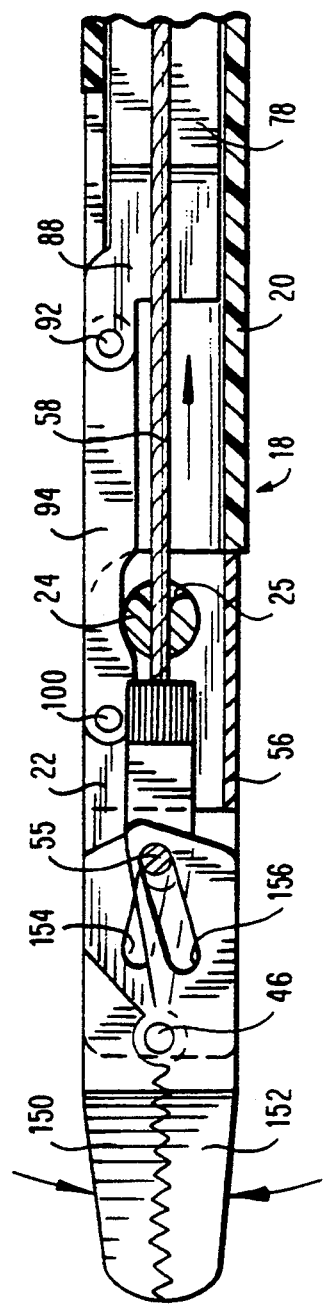
FIG. 13 is a side cross sectional view of the tool head shown in FIG. 11 in a closed position.

The fixed tubular section 20 of endoscopic portion 18 is formed with a longitudinal slot 42 extending proximally from the distal end 26 thereof. Slot 42 is particularly adapted for enabling the pivotal movement of articulating section 22 about pivot pin 24. An aperture 44 is provided adjacent distal end 26 for maintaining the pivot pin 24. Pivot pin 24 is provided with a transverse diverging bore hole 25, which is best seen in FIG. 4. A circumferential groove 45 is formed in the tubular section 20 adjacent the proximal end 27 thereof for enabling tubular section 20 to be securely mounted in the stepped bore 40 of handle portion 12.

The tool head 28 which depends from articulating section 22 includes cooperating jaws 30, 32, shown here in a clamp configuration. Jaws 30, 32 pivot about a pin 46 which passes through apertures 48, 50 in jaws 30, 32, respectively and through aperture 52 formed in articulating section 22. Jaws 30, 32 also include camming slots 53, 54 respectively formed in the proximal ends thereof for receiving a camming pin 55. Pin 55 is mounted in a yoke 56 and is adapted for reciprocal coaxial movement within the fixed section 20 of endoscopic portion 18. A flexible cable 58 having opposed proximal and distal ends 60 and 62 is mounted, at the distal end 62 thereof, to yoke 56, and at the proximal end 60 thereof, to the distal end 64 of a plunger member 66. Plunger member 66 includes a head portion 68 which is retained in a pivotal clip assembly 70 having opposed complimentary sections 72 and 74. Opposed clip sections 72 and 74 are mounted to one another and are disposed within a port 76 formed in the pivoting handle 16 of handle portion 12. Movements of pivoting handle 16 thus causes corresponding coaxial movements of plunger member 66.

Figure 3:
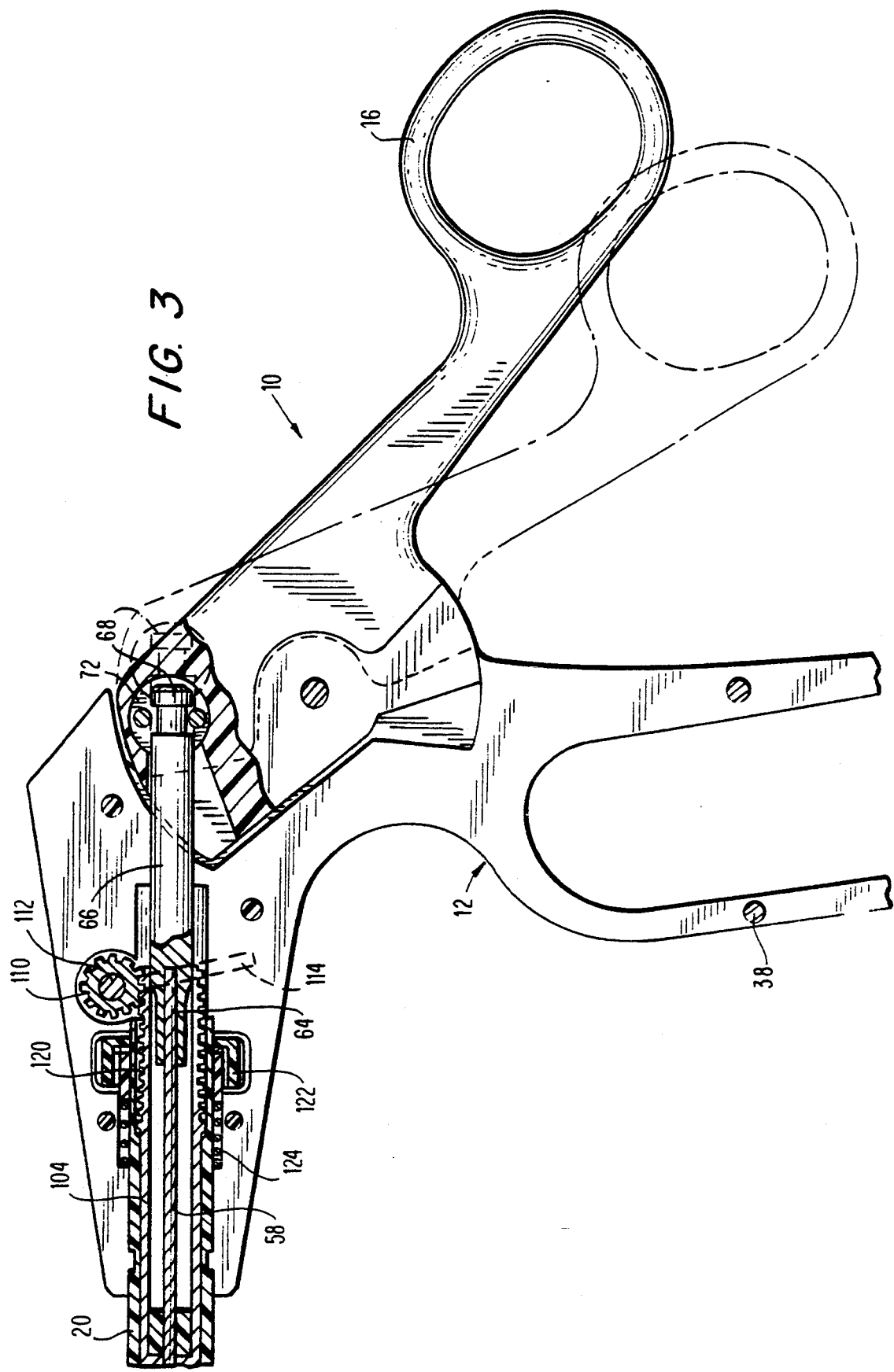
FIG. 3 is a side cross-sectional view taken along line 3—3 of FIG. 1 illustrating the handle portion of the endoscopic surgical instrument.

Referring now to FIGS. 2 and 3, the endoscopic surgical instrument 10 of the subject invention further includes a linkage assembly which is associated with the endoscopic portion 18 and handle portion 12 for pivoting the articulating portion 22 thereof. The linkage assembly includes an elongated push rod 78 having opposed proximal and distal ends 80 and 82, with the proximal end 80 thereof being formed with an aperture 84 for receiving a pin 86. In addition, rod 78 includes a mounting flange 88 provided on the distal end 82 thereof which includes an aperture 90 for receiving a pin 92. Pin 92 functions to pivotally connect a link rod 94 to mounting flange 88 through an aperture 96 disposed in the proximal end of link rod 94. Link rod 94 is provided with an aperture 98 in the distal end thereof, through which a pin 100 extends to be pivotally mounted in an aperture 102 which is provided in articulating section 22 of endoscopic portion 18. The linkage mechanism of the subject invention further includes an elongated gear rack member 104 which is capable of being reciprocated in an axial direction. Gear rack member 104 is formed with circumferential gear teeth 106 and an axial bore 107 which is provided to permit flexible cable 58 to extend through so as to reach plunger member 66. Gear rack member 104 is further provided with a mounting flange 108 having an aperture 109. Pin 86 extends through aperture 109 and is mounted in aperture 84 so as to connect rack member 104 to the proximal end 80 of push rod 78. An annular pinion gear 110 is mounted on a shaft 112 associated with handle portion 12. Pinion gear 110 meshes with the circumferential gear teeth 106 on rack member 104. Rotation of pinion gear 110 is achieved by rotating a pair of opposed wing members 114 and 116 which are mounted on the opposed ends of shaft 112.

The endoscopic surgical instrument 10 of the subject invention further comprises a mechanism for rotating the endoscopic portion 18 about its longitudinal axis relative to handle portion 12. This mechanism comprises an annular bushing 120 that is concentrically mounted within a rotatable collar 122 mounted within the stepped bore 40 formed in handle portion 12. Bushing 120 is maintained against collar 122 by a coiled spring 124 disposed in a section of bore 40. Spring 124 acts to bias bushing 120 toward the proximal end of the surgical instrument 10. The proximal end 27 of fixed section 20 of endoscopic portion 18 extends through bushing 120 and is mounted therein for rotation.

Referring to FIGS. 3–6, the operation of the cooperating jaws 30 and 32 of tool head 28 is accomplished by moving the pivoting handle 16 as shown in FIG. 3. Upon moving the pivoting handle 16, the head 68 of plunger member 66 travels axially causing cable 58 to translate. In order to close the cooperating jaws 30 and 32, which are normally open as illustrated in FIG. 4, the pivoting handle 16 is squeezed by the surgeon, thereby causing the plunger member 66 to pull cable 58 in a proximal direction. The movement of cable 58 causes a corresponding axial movement of yoke 56, as shown by the indicator arrow in FIG. 6. In particular, the movement of yoke 56 causes pin 55 to cam proximally within slots 53 and 54 of jaws 30 and 32 respectively, so as to cause jaws 30 and 32 to close. Turning now to FIGS. 7–10, the pivoting movement of the articulating section 22 of endoscopic portion 18 is accomplished by rotating wing members 114 and 116 to a desired angular position. More particularly, a detent engaging member 118 is coaxially mounted on shaft 112 along with wing members 114 and 116 which can be rotatably engaged in various predetermined positions indicated on handle portion 12 which correspond to 30°, 60°, or 90° of rotation depending upon the surgical procedure being preformed.

To pivot the tool head 28 angularly with respect to the longitudinal axis of the endoscopic portion 18, the wing members 114 and 116 are rotated in a counter-clockwise direction. This counter-clockwise rotation causes pinion gear 110 to rotate on shaft 112 in a counter-clockwise direction. Simultaneously, gear rack member 104 advances proximally within stepped bore 40 causing the elongated push rod 78 to advance proximally along the longitudinal axis of encloseopic portion 18. Link member 94 is pulled in a generally proximal direction, as shown by the indicator arrow running parallel to link member 94 in FIG. 7, causing the articulating section 22, and the associated tool head 28, to pivot in an angular direction about pin 24. Once the articulating section 22 is in a desired angular position relative to the longitudinal axis of endoscopic portion 18, the cooperating jaws 30 and 32 may be opened or closed by operating the pivoting handle 16 in handle portion 12 as discussed previously.

Turning now to FIGS. 11–15, an alternate embodiment of the tool head 28 of the endoscopic surgical instrument 10 of the subject invention is illustrated. In this embodiment, the tool head 28 includes cooperating dissector jaws 150, 152 which are pivotally mounted on the articulating section 22 of endoscopic portion 18. Furthermore, dissector jaws 150, 152 are provided with camming slots 154, 156 respectively formed in the distal ends thereof. As in the preferred embodiment, camming pin 55 is accommodated within slots 154, 156 and slides in response to axial movements of yoke member 56 when the pivoting handle 16 is operated to open and close jaws 150 and 152.

Referring to FIGS. 14 and 15, when link rod 94 is moved in a generally proximal direction, tool head 28 pivots relative to the longitudinal axis of endoscopic portion 18. Upon reaching a desired angular position, the cooperating dissector jaws 150 and 152 may be opened or closed by operating pivoting handle 16 of handle portion 12. Moreover, when pivoting handle 16 is operated, cable 58, which extends through the diverging bore 25 formed in pivot pin 24, pulls on yoke member 56 causing pin 55 to slide within slots 154 and 156, thereby opening or closing the dissector jaws 150 and 152.

Figure 16:
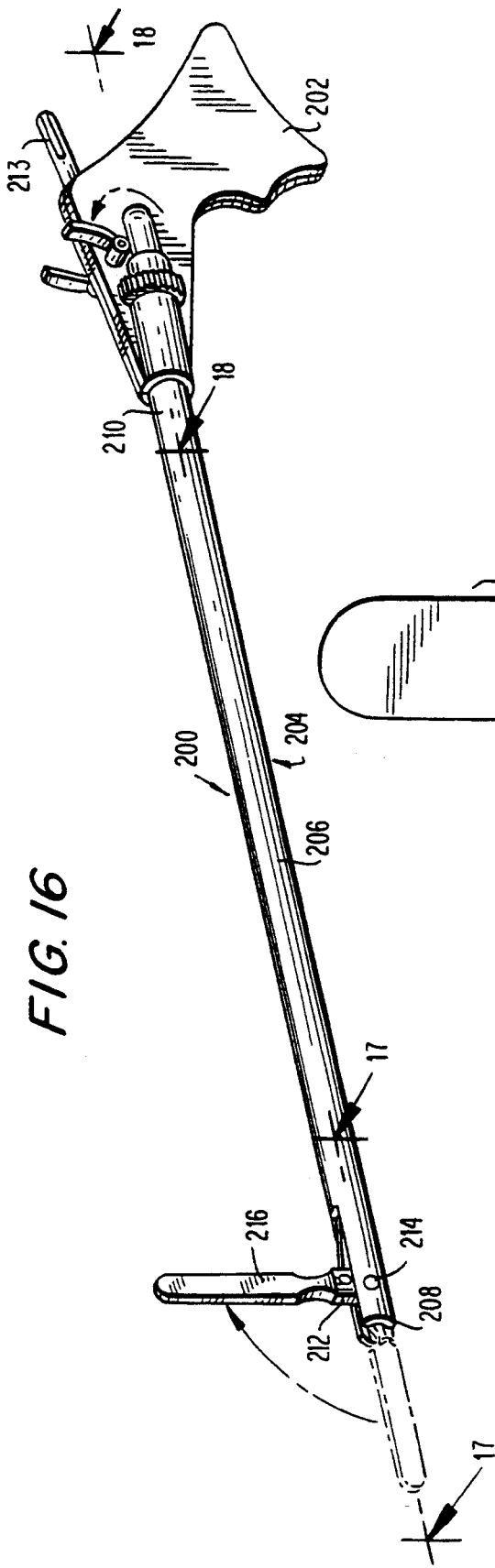
FIG. 16 is a perspective view of an alternate embodiment of the subject invention which includes an articulating paddle for performing retraction tasks.

Turning now to FIG. 16, an alternate endoscopic surgical instrument 200 of the subject invention is illustrated. Surgical instrument 200 comprises a handle portion 202 configured as a pistol-grip, and an endoscopic portion 204. Endoscopic portion 204 includes a fixed tubular section 206 having opposed distal and proximal ends 208 and 210, and an articulating section 212 which is pivotally connected to the fixed section 206 by a pivot pin 2 14 disposed adjacent to the distal end 208 thereof. Surgical instrument 200 further comprises an elongated paddle 216 which depends from articulating section 212 and which is intended for use as a retractor tool during surgical procedures.

An electrocautery connector 213 is provided and extends from the handle portion 202 for cauterization of tissue at the surgical site during the surgical procedure. The connector 213 is in electrical connection with the tool 216. In order to protect the surgeon who is using the device from electrical shock, the handle 202 is preferably constructed of a rigid non-conducting material which renders the apparatus lightweight and electrically insulated.

Figure 17:
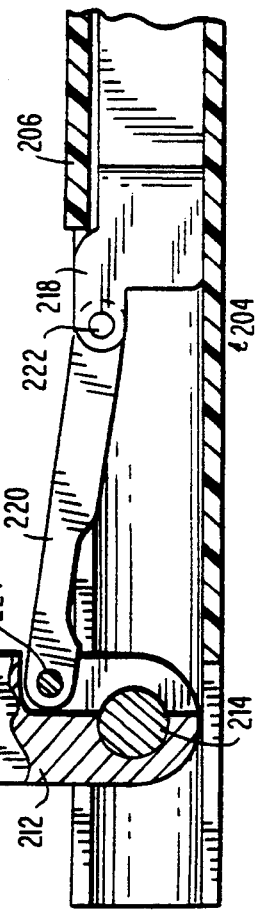
FIG. 17 is a side cross-sectional view taken along line 17—17 of FIG. 16.

Referring to FIG. 17, surgical instrument 200 is provided with a linkage assembly that is similar to the assembly provided in the preferred embodiment of the subject invention. It comprises an elongated push rod 2 18 which is pivotally connected to a link member 220 by a pin 222. Link member 220 is pivotally connected to articulating section 212 by a pin 224. Referring to FIG. 18, the linkage assembly also includes an annular pinon gear 226 which is mounted for rotation on a shaft 228 provided in handle portion 202. Wing members 230 are coaxially mounted on shaft 228 for rotating pinon gear 226. Pinon gear 226 meshes with a reciprocating gear rack member 232 disposed within the stepped bore 234 which is formed in handle portion 202. Furthermore, gear rack member 232 is connected to elongated push rod 218.

Surgical instrument 200 also includes an assembly for rotating the endoscopic portion 204 about its longitudinal axis. The rotating assembly includes an annular collar 236 which is disposed within a port 238 formed in bore 234, and an annular bushing 240 concentrically disposed within the annular collar 236. Bushing 240 is provided for accommodating the proximal end of endoscopic portion 206, which is mounted therein for rotation. A coiled spring 242 is disposed within stepped bore 234 for biasing bushing 240 in a proximal direction so as to maintain it within collar 236.

Referring now to FIG. 19, to lower the retractor paddle 216 into a position parallel to the longitudinal axis of endoscopic portion 204, the wing members 230 are rotated in a clockwise direction. This clockwise rotation of wing members 230 causes a clockwise rotation of pinion gear 226 about shaft 228. Consequently, gear rack member 232 is caused to advance distally along the axis of endoscopic portion 204. Push rod 218 advances distally within the fixed section 206 of endoscopic portion of 204. Upon advancing, push rod 218 causes link member 220 to move in a generally distal direction, thereby causing paddle 216 to pivot downwardly, as shown by the indicator arrow in FIG. 19.

Figure 20:
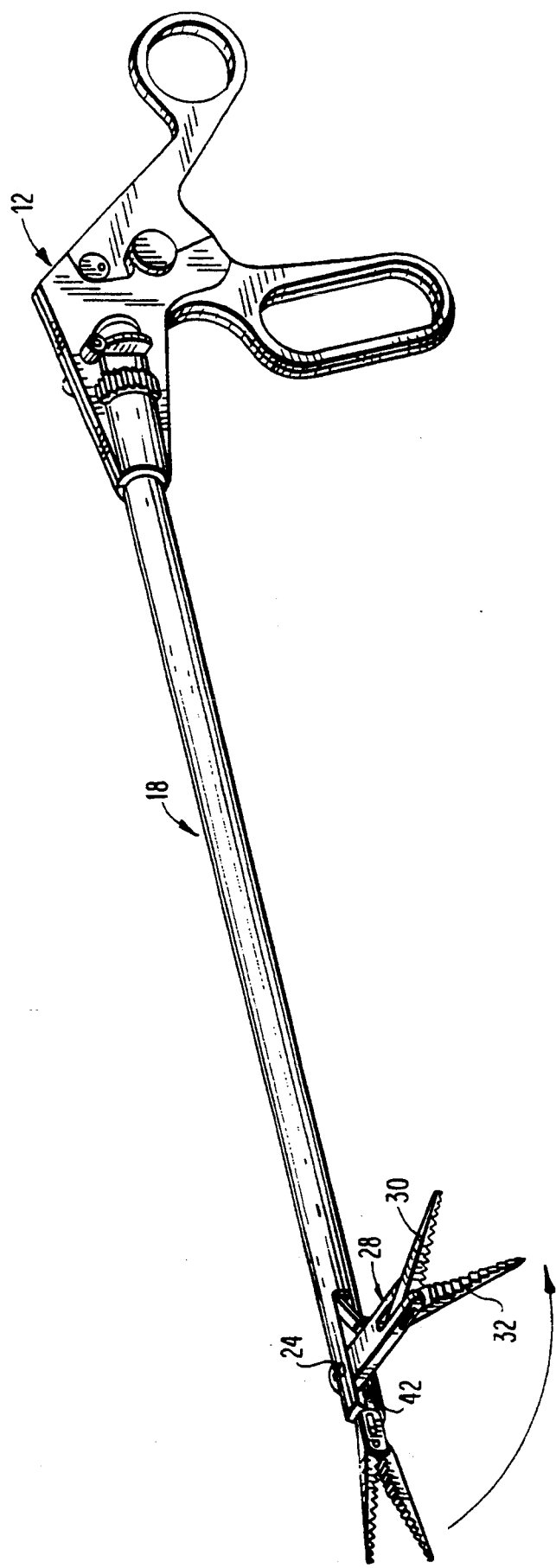
FIG. 20 is a perspective view of another embodiment of the articulating endoscopic surgical instrument of the subject invention.
Figure 21:
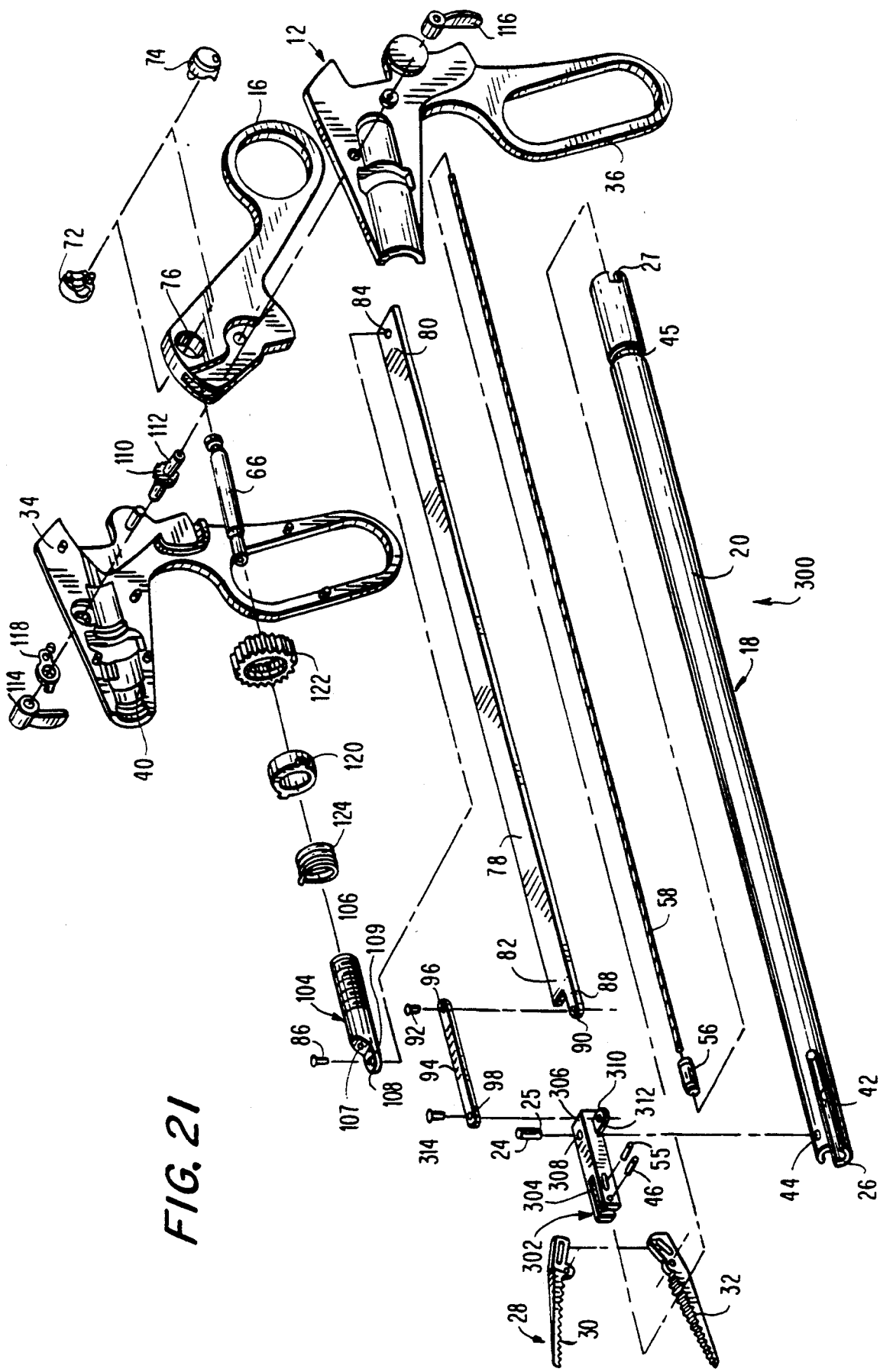
FIG. 21 is an exploded view of the articulating endoscopic surgical instrument of FIG. 20.

Turning to FIGS. 20 and 21, an alternate endoscopic surgical instrument 300 of the subject invention is illustrated. Surgical instrument 300 is structurally similar to the preferred embodiment of the subject invention. However, the range of operability of the tool head 28 of surgical instrument 300 is distinct in that it can be pivoted in a horizontal plane with respect to the endoscopic portion 18 of surgical instrument 300.

In this embodiment, the components and function of the linkage assembly remains essentially the same as in the preferred embodiment. In particular. annular pinion gear 110 which is mounted on a shaft 112 in handle portion 12, meshes with the circumferential gear teeth 106 of gear rack member 104. The proximal end 80 of the elongated push rod 78 is pivotally connected to the flange 108 of gear rack member 104 and the distal end 82 of the elongated push rod 78 is pivotally connected to link member 94 by a pin 92. The linkage assembly of surgical instrument 300 is operatively connected to an articulating section 302. Articulating section 302 includes a slotted distal portion 304 and a proximal portion 306 having a bore 308 for receiving pivot pin 24. A cleat 3 10 extend outwardly from the proximal portion 306 of articulating section 302 and includes an aperture 312 for receiving a pivot pin 314 which connects the link member 94 to the articulating section 302.

To pivot the tool head 28 angularly, in a horizontal plane, with respect to the longitudinal axis of the endoscopic portion 18, the wing members 114 and 116 are rotated. Simultaneously, gear rack member 104 advances within stepped bore 40 causing the elongated push rod 78 to advance along the longitudinal axis of endoscopic portion 18. Movement of the elongated push rod 78 causes link member 94 to pivot in such a manner so as to cause the articulating section 302, and the associated tool head 28, to pivot in an angular direction about pivot pin 24. Once the articulating section 302 is in a desired angular position relative to the longitudinal axis of endoscopic portion 18, the cooperating jaws 30 and 32 may be operated by manipulating the pivoting handle 16 in handle portion 12 as discussed hereinabove.

The endoscopic surgical instrument of the subject invention is compact, lightweight and easy to use. It is intended to enable the surgeon to use the instrument with one hand, thus freeing the other hand for performance of other surgical tasks.

To the extent not already indicated, it also will be understood by those of ordinary skill in the art that any one of the various specific embodiments herein described and illustrated may be further modified to incorporate features shown in other of the specific embodiments.

Although the endoscopic surgical instrument of the subject invention has been described with respect to a preferred embodiment, it is apparent that changes may be made to the invention without departing from the spirit and scope of the invention as defined by the appended claims.

What is claimed is:

1. An endoscopic surgical apparatus comprising:
   a handle portion;
   an endoscopic portion including an elongated tubular section defining a longitudinal axis and having opposed proximal and distal ends, the proximal end of said tubular section extending from said handle portion, and an articulating section pivotally connected to said tubular section adjacent the distal end thereof;
   tool means depending from said articulating section of said endoscopic portion for performing a surgical task;
   a linkage mechanism including at least one reciprocating member associated with said handle portion and said endoscopic portion for pivoting said articulating section to an articulated position at an angle to the longitudinal axis of said tubular section; and means for actuating said tool means at least when said articulating section is disposed at an angle to said longitudinal axis of said tubular section.

2. A surgical apparatus as recited in claim 1 wherein said articulating section is pivotable about a pivot point within a 90° sector of rotation.

3. A surgical apparatus as recited in claim 1 wherein said linkage mechanism comprises a plurality of reciprocating members operable by a rotating member disposed in said handle portion to control the movement of said articulating section.

4. A surgical apparatus as recited in claim 3 wherein said plurality of reciprocating members includes first, second, and third reciprocating members.

5. A surgical apparatus as recited in claim 4 wherein said rotating member includes an annular pinion gear mounted for rotation in said handle portion and said first reciprocating member is formed with a gear rack for meshing with said pinion gear, said first reciprocating member being movable along the longitudinal axis of said endoscopic portion in response to rotation of said pinion gear.

6. A surgical apparatus as recited in claim 5 wherein said second reciprocating member is an elongated push rod extending through said tubular section having opposed proximal and distal ends, the proximal end of which is connected to said first reciprocating member, said push rod being movable in an axial direction in response to axial movements of said first reciprocating member.

7. A surgical apparatus as recited in claim 6 wherein said third reciprocating member is a link rod having opposed ends with one of said ends pivotally connected to the distal end of said push rod and the opposed end pivotally connected to said articulating section of said endoscopic portion.

8. A surgical apparatus as recited in claim 7 wherein rotation means are included in said handle portion for revolving said endoscopic portion about the longitudinal axis thereof.

9. A surgical apparatus as recited in claim 8 wherein said rotation means comprises a rotatable annular collar and an annular bushing coaxially mounted in said rotatable collar and adapted for engaging the proximal end of said fixed section of said endoscopic portion.

10. A surgical apparatus as recited in claim 9 wherein an electrocautery connector is mounted in said handle portion for cauterization of tissue at a surgical site.

11. A surgical apparatus as recited in claim 10 wherein said tool means is a paddle for performing retraction tasks.

12. A surgical apparatus as recited in claim 10 wherein said handle portion includes a fixed handle and a pivoting handle.

13. A surgical apparatus as recited in claim 12 wherein said tool means comprises a pair of cooperating jaws for performing grasping tasks.

14. A surgical apparatus as recited in claim 13 wherein said cooperating jaws are operatively connected to said pivoting handle.

15. A surgical apparatus as recited in claims 14 wherein said cooperating jaws and said pivoting handle are operatively connected to one another by a flexible cable assembly.

16. A surgical apparatus comprising:

a handle portion including at least one pivoting handle;

an endoscopic portion including an elongated tubular section defining a longitudinal axis and having opposed proximal and distal ends, the proximal end of said tubular section extending from said handle portion, and an articulating section pivotally connected to said tubular section adjacent the distal end thereof;

a pair of cooperating jaws depending from said articulating section of said endoscopic portion;

a linkage mechanism associated with said handle portion and said endoscopic portion for pivoting said articulating section to an articulated position at an angle to the longitudinal axis of said tubular section;

rotation means for rotating said cooperating jaws about the longitudinal axis of said endoscopic portion relative to said handle portion; and means for operatively connecting said cooperating jaws and said at least one pivoting handle, whereby movement of said at least one pivoting handle will cause said cooperating jaws to open and close.

17. A surgical apparatus as recited in claim 16 wherein said connecting means comprises a cable assembly.

18. A surgical apparatus as recited in claim 16 wherein said articulating section is pivotable about a pivot point within a 90 ° sector of rotation.

19. A surgical apparatus as recited in claim 16 wherein said linkage mechanism comprises a plurality of reciprocating members operable by a rotating member disposed in said handle portion to control the movement of said articulating section.

20. A surgical apparatus as recited in claim 19 wherein said plurality of reciprocating members includes first, second, and third reciprocating members.

21. A surgical apparatus as recited in claim 20 wherein said rotating member includes an annular pinion gear mounted for rotation in said handle portion and said first reciprocating member is formed with a gear rack for meshing with said pinion gear, said first reciprocating member being movable along the longitudinal axis of said endoscopic portion in response to rotation of said pinion gear.

22. A surgical apparatus as recited in claim 21 wherein said second reciprocating member is an elongated push rod extending through said tubular section having opposed proximal and distal ends, the proximal end of which is connected to said first reciprocating member, said push rod being movable in an axial direction in response to axial movements of said first reciprocating member.

23. A surgical apparatus as recited in claim 22 wherein said third reciprocating member is a link rod having opposed ends with one of said ends pivotally connected to the distal end of said push rod and the opposed end pivotally connected to said articulating section of said endoscopic portion.

24. A surgical apparatus as recited in claim 23 wherein said rotation means comprises a rotatable annular collar and an annular bushing coaxially mounted in said rotatable collar and adapted for engaging the proximal end of said fixed section of said endoscopic portion.

25. A surgical apparatus as recited in claim 24 wherein a spring is mounted in said handle portion for maintaining said annular bushing within said rotatable collar.

26. A surgical apparatus comprising:

a handle portion;

an endoscopic portion including an elongated tubular section defining a longitudinal axis and having opposed proximal and distal ends, the proximal end of said tubular section extending from said handle portion, and an articulating section pivotally connected to said tubular section adjacent the distal end thereof;

tool means depending from said articulating section of said endoscopic portion for performing surgical tasks;

a linkage mechanism associated with said handle portion and said endoscopic portion for pivoting said articulating section to an articulated position at an angle to the longitudinal axis of said tubular section; and rotation means for rotating said endoscopic portion about the longitudinal axis thereof relative to said handle portion.

27. A surgical apparatus as recited in claim 26 wherein said tool means comprises retractor means for performing retraction tasks.

28. A surgical apparatus as in claim 27 wherein said retractor memos comprises at least one paddle depending from said articulating section.

29. A surgical apparatus as recited in claim 26 wherein said articulating section is pivotable about a pivot point within a 90° sector of rotation.

30. A surgical apparatus as recited in claim 27 wherein said linkage mechanism comprises a plurality of reciprocating members operable by a rotating member disposed in said handle portion to control the movement of said articulating section.

31. A surgical apparatus as recited in claim 30 wherein said plurality of reciprocating members includes first, second, and third reciprocating members.

32. A surgical apparatus as recited in claim 31 wherein said rotating member includes an annular pinion gear mounted for rotation in said handle portion and said first reciprocating member is formed with a gear rack for meshing with said pinion gear, said first reciprocating member being movable along the longitudinal axis of said endoscopic portion in response to rotation of said pinion gear.

33. A surgical apparatus as recited in claim 32 wherein said second reciprocating member is an elongated push rod extending through said tubular section having opposed proximal and distal ends, the proximal end of which is connected to said first reciprocating member, said push rod being movable in an axial direction in response to axial movements of said first reciprocating member.

34. A surgical apparatus as recited in claim 33 wherein said third reciprocating member is a link rod having opposed ends with one of said ends pivotally connected to the distal end of said push rod and the opposed end pivotally connected to said articulating section of said endoscopic portion.

35. A surgical apparatus as recited in claim 34 wherein said rotation means comprises a rotatable annular collar and an annular bushing coaxially mounted in said rotatable collar and adapted for engaging the proximal end of said fixed section of said endoscopic portion.

36. A surgical apparatus as recited in claim 35 wherein a coiled spring is mounted in said handle portion for maintaining said annular bushing within said rotatable collar.

37. An endoscopic surgical apparatus comprising:

a handle portion;

an endoscopic portion including an elongated tubular section defining a longitudinal axis and having opposed proximal and distal ends, the proximal end of said tubular section extending from said handle portion, and an articulating section pivotally connected to said tubular section adjacent the distal end thereof;

jaw means depending from said articulating section of said endoscopic portion for performing a surgical task;

a linkage mechanism including at least one reciprocating link member extending from said handle portion through said endoscopic portion for pivoting said articulating section relative to the longitudinal axis of said tubular section; and means cooperating with said handle portion for moving said jaw means between open and closed positions.

38. An endoscopic surgical apparatus comprising:

a handle portion;

an endoscopic portion including an elongated tubular section defining a longitudinal axis and having opposed proximal and distal ends, the proximal end of said tubular section extending from said handle portion and an articulating section movably connected to said distal end of said tubular section;

tool means operatively connected to said articulation section adjacent a distal end thereof;

a linkage mechanism including a plurality of reciprocating link members associated with said handle portion and said endoscopic portion for pivoting said tool means about an axis transverse to the longitudinal axis of said tubular section to a predetermined number of positions; and means disposed at least partially within said endoscopic portion for actuating said tool means.

39. A surgical apparatus comprising:

a handle portion;

an endoscopic portion including an elongated tubular section defining a longitudinal axis and having opposed proximal and distal ends, the proximal end of said tubular section extending from said handle portion and an articulating section pivotably connected to said distal end of said tubular section;

retractor means extending from said articulating section adjacent a distal end thereof for performing a surgical task;

means associated with said handle portion and said endoscopic portion for pivoting said articulating section about an axis orthogonal to the longitudinal axis of said tubular section; and means for rotating said retractor means about said longitudinal axis of said tubular section relative to said handle portion.

40. An apparatus as recited in claim 39 wherein said pivoting means comprises a linkage mechanism.

41. An apparatus as recited in claim 39, further comprising means for controlling movement of said retractor means.

42. An apparatus as recited in claim 41 wherein said pivoting means comprises a linkage mechanism.

43. An apparatus as recited in claim 41 wherein said articulating section is pivotable about a pivot point within a 90° sector of rotation.

44. An apparatus as recited in claim 39, further comprising means for rotating said retractor means about the longitudinal axis of said endoscopic portion.

45. An endoscopic surgical apparatus comprising:

a handle portion;

an endoscopic portion including an elongated tubular section defining a longitudinal axis and having opposed proximal and distal ends, the proximal end of said tubular section extending from said handle portion, and an articulating section pivotally connected to said tubular section by a horizontally oriented pivot pin disposed adjacent the distal end thereof;

tool means depending from said articulating section of said endoscopic portion for performing a surgical task;

a reciprocating linkage mechanism including at least one link member associated with said handle portion and said endoscopic portion for pivoting said articulating section to an articulated position about an axis orthogonal to the longitudinal axis of said tubular section; and means for actuating said tool means at least when said articulating section is disposed at an angle to said longitudinal axis of said tubular section.

46. An endoscopic apparatus comprising:

a handle portion;

an endoscopic portion including an elongated tubular section defining a longitudinal axis and having opposed proximal and distal ends, the proximal end of said tubular section extending from said handle portion, and an articulating section pivotally connected to said tubular section by a vertically oriented pivot pin disposed adjacent the distal end thereof;

a retractor mechanism depending from said articulating section of said endoscopic portion for performing a surgical task; and a linkage mechanism including at least one reciprocating member associated with said handle portion and said endoscopic portion for pivoting said articulating section to an articulated position about an axis orthogonal to the longitudinal axis of said tubular section.

47. A surgical apparatus as recited in claim 1 wherein said retractor mechanism includes at least one retractor member.

* * * * *